(12) United States Patent
Oddsson et al.

(10) Patent No.: US 7,618,463 B2
(45) Date of Patent: Nov. 17, 2009

(54) ENERGY RETURNING PROSTHETIC JOINT

(75) Inventors: Magnus Oddsson, Hafnarfjordur (IS); Vilhjalmur Freyr Jonsson, Reykjavik (IS); Christophe Guy Lecomte, Reykjavik (IS)

(73) Assignee: Össur hf, Reykjavik (IS)

( * ) Notice: Subject to any disclaimer, the term of this patent is extended or adjusted under 35 U.S.C. 154(b) by 517 days.

(21) Appl. No.: 11/483,676

(22) Filed: Jul. 11, 2006

(65) Prior Publication Data
US 2007/0021842 A1    Jan. 25, 2007

Related U.S. Application Data

(60) Provisional application No. 60/697,552, filed on Jul. 11, 2005, provisional application No. 60/794,823, filed on Apr. 26, 2006.

(51) Int. Cl.
A61F 2/64    (2006.01)
(52) U.S. Cl. ........................................................ 623/46
(58) Field of Classification Search .............. 623/39–46
See application file for complete search history.

(56) References Cited

U.S. PATENT DOCUMENTS

| | | | |
|---|---|---|---|
| 5,545,232 A | 8/1996 | Van de Veen | |
| 5,695,527 A | 12/1997 | Allen | |
| 5,720,471 A | 2/1998 | Constantinescu et al. | |
| 5,746,773 A | 5/1998 | Littig | |
| 5,799,760 A | 9/1998 | Small | |
| 5,800,567 A | 9/1998 | Cooper et al. | |
| 5,800,568 A | 9/1998 | Atkinson et al. | |
| 5,897,594 A | 4/1999 | Martin et al. | |
| 6,350,286 B1 | 2/2002 | Atkinson et al. | |
| 6,355,071 B1 | 3/2002 | Cheng | |
| 6,562,075 B2 | 5/2003 | Townsend et al. | |
| 7,288,118 B1 * | 10/2007 | Swanson, Sr. | 623/46 |
| 2005/0203638 A1 | 9/2005 | Slemker et al. | |
| 2006/0167546 A1 * | 7/2006 | Bartlett | 623/11.11 |

OTHER PUBLICATIONS

"Are You Ready"; FirstStep; pp. 34-57 (undated).
"Prosthetic Knee Designs: Biomechanics and Functional Classification"; International Fellow in Paediatric Orthopaedic Surgery, Atlanta Scottish Rite Hospital, Georgia, USA; Damian McCormack; (undated).
"Critical Biomechanical Principles," date unknown, [online],[retrieved Apr. 27, 2005]. Retrieved from the Internet: http://www.footmaxx.com/clinicians/principles.html.
"National Amputee Centre: Prosthetic Knees," The War Amps: Artificial Limbs—Prosthetic Knees, 2005 [online], [retrieved Jun. 29, 2005]. Retrieved from the Internet: http://www.waramps.ca/nac/knees.html Also at ...knees1.html through ...knees7.html.
"inMotion: Prosthetic Primer: Prosthetic Knees," vol. 9, Issue 6, Nov./Dec. 1999, [online], [retrieved Jun. 29, 2005]. Retrieved from the internet: http://www.amputee-coalition.org/Inmotion/nov_dec_99/knees.html.

(Continued)

Primary Examiner—Bruce E Snow
(74) Attorney, Agent, or Firm—Bacon & Thomas, PLLC

(57) ABSTRACT

An energy returning prosthetic joint arranged for use as a knee joint in prosthetic limbs includes a biasing or spring member connected to upper and lower attachment members. The spring member includes a composite material having an energy returning property. A cushion may be provided within the range of curvature of the spring member, or be connected to frame members in order to limit motion of the spring member.

16 Claims, 5 Drawing Sheets

OTHER PUBLICATIONS

"BCL-Design of a Carbon Fiber/Epoxy Spring for Use in a Prosthetic Knee Replacement by Mickey Reilley," date unknown, [online], [retrieved on Sep. 19, 2005]. Retrieved from the Internet: http://bcl.me.berkeley.edu/students_topics/st14/st14.html.

"A Comparison of Current Biomechanical Terms," JPO 1990; vol. 2, No. 2, p. 107, [online], [retrieved on Feb. 3, 2006]. Retrieved from the Internet: http://www.oandp.org/jpo/library/printArticle.asp?printArticleID=1990_02_107.

"Design Principles, Biomechanical Data and Clinical Experience with a Polycentric Knee Offering Controlled Stance Phase Knee Flexion: A Preliminary Report," JPO 1997; vol. 9, No. 1, p. 18; [online], [retrieved on Feb. 7, 2006], Retrieved from the Internet: http://www.oandp.org/jpo/library/printArticle.asp-?printArticleld=199701018.

\* cited by examiner

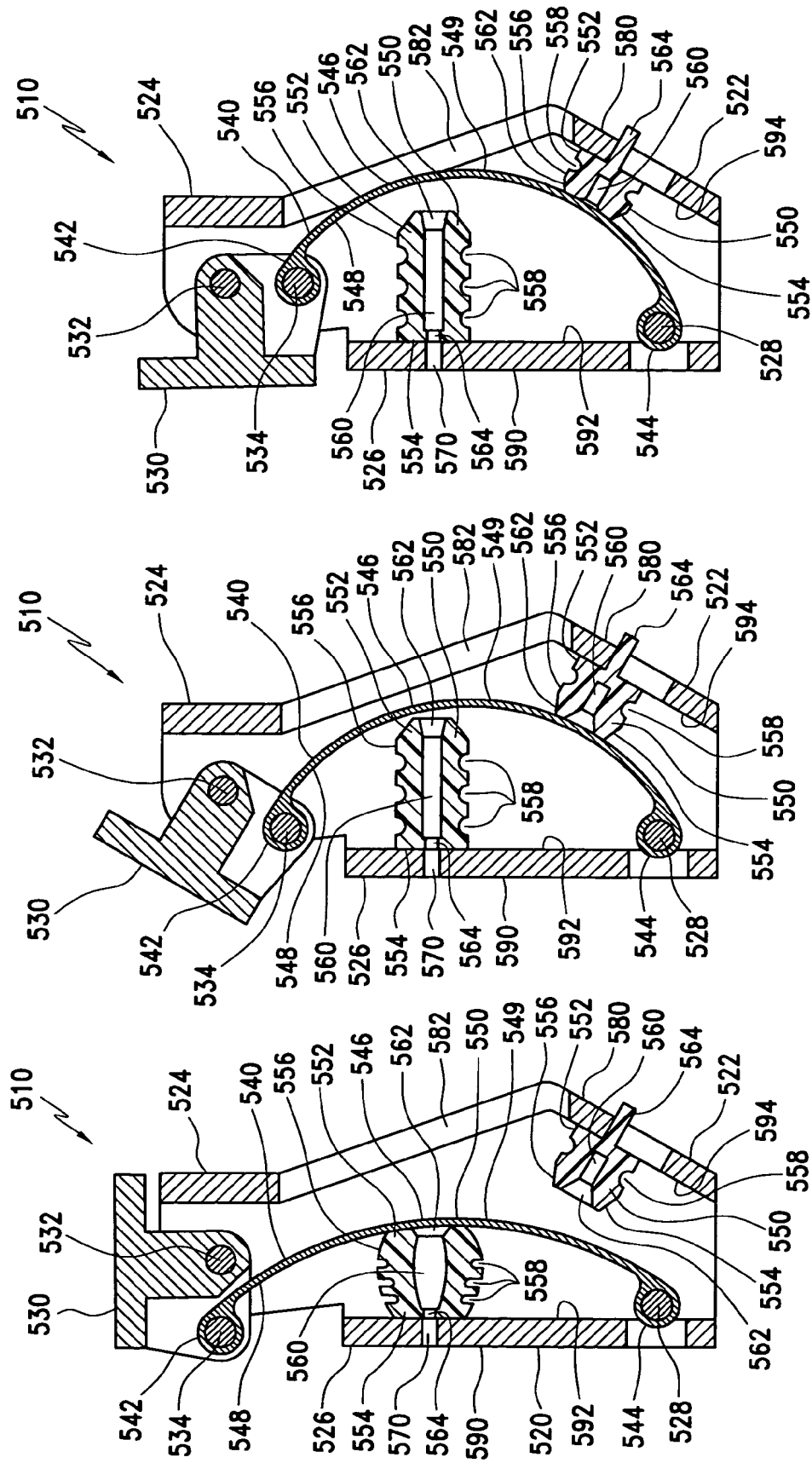

ENERGY RETURNING PROSTHETIC JOINT

This application claims the benefit of U.S. provisional application No. 60/697,552 filed on 11 Jul. 2005, and U.S. provisional application No. 60/794,823 filed on 26 Apr. 2006.

FIELD OF THE INVENTION

The present invention relates generally to the field of prosthetic limbs, and more particularly to a prosthetic joint.

BACKGROUND

Artificial limbs, including leg prostheses, employ a wide range of technologies to provide solutions suitable to many differing needs. For a trans-femoral amputee, basic needs in a leg prosthesis include stability, while standing and during the stance phase of a walking gait, and mechanical compatibility with the walking (or running) gait and some manner of knee flexion during stance and swing phases of a gait.

Certain trade-offs exist between stability, and walking or running performance. A simple, non-articulable leg (having no movable knee), for example, may provide maximum stability, but does not provide for an ideal gait. Also, sitting may be awkward if a person cannot bend their knee.

For people having lost their biological knees, it is important that the prosthetic joint functions properly and is reliable. There are numerous types of prosthetic joint designs available, each having its benefits and shortcomings.

A widely used prosthetic joint design is of a single axis type. The single axis knee employs a simple hinge at the level of the anatomical knee. Such a simple design results in low cost, light weight, and durability. However, little gait assistance is provided to the amputee by the limb itself; the amputee is required to expend a certain degree of muscle power to help to control and stabilize the prosthetic leg.

The single axis knee may be configured with a fluid control unit to increase or decrease the swing phase resistance as one speeds up and slows down. Yet by adding the fluid control unit, the cost of the knee and complexity of the knee are greatly increased.

In accordance with another type of prosthetic joint, a polycentric knee design employs a mechanically complex plurality of hinge or rotation points that allow variations in the action of the knee through the gait, typically providing increased stability early in the stance phase while allowing easy bending during the swing phase and while sitting. Additional mechanical complexity is often found in the form of air or hydraulic cylinders that vary swing phase resistance or flexion during variations in the gait, or provide for shock absorption. Microprocessor controllers may be employed to measure aspects of the gait to control operation of the air or hydraulic cylinders or other components of the knee.

Of course, because of the complexity of the polycentric knee design, this design is not as reliable as the single hinge design. Moreover, this design costs substantially more to produce than the single hinge design due to its additional moving parts.

Other highly complex mechanical (and in some cases microprocessor controlled) prosthetic joints have evolved to improve the performance of leg prostheses. Current prosthetic joints are often a complicated system including joints, arms, bearings, cylinders, and other mechanical and electro-mechanical components. Further, some employ sophisticated electronics including microprocessor circuits and instrumentation of the various parts of the knee.

The complexity of such prosthetic joints tends to adversely affect the potential life of the knee as well as security to the user, as the parts are subject to wear. Moreover, with increased mechanical and electronic complexity comes the need for increased maintenance and tuning to achieve or maintain proper function.

It is therefore desirable to provide a prosthetic joint that provides improved functionality, user security, and performance in a simplified structure having few moving parts, and that can be produced at low cost.

SUMMARY

In order to overcome the shortcomings of known prosthetic joints, different embodiments are provided which pertain to an inventive joint that can be used in a prosthetic leg.

In one embodiment, a prosthetic joint is constructed from a material having an energy returning property. The knee has a base portion configured in a substantially planar shape, an arcuate portion having a first end connected to the base portion, and an asymmetrical curvilinear portion connected to a second end of the arcuate portion and extending obliquely relative to the base portion. A first attachment member is securable onto the base portion and a second attachment member is securable onto the curvilinear portion. Each of the attachment members includes a locking feature provided for coupling the upper and lower portions of the prosthetic leg. The locking features of the first and second attachment members are axially aligned with one another.

In another embodiment, the knee is a spring member formed from a material having an energy returning property. The knee defines an upper curved portion connected to a lower curved portion. An upper base portion is provided that extends from the upper curved portion preferably in a substantially planar configuration. A lower base portion is provided that extends from the lower curved portion preferably in a substantially planar configuration.

The upper and lower curved portions are preferably asymmetrical, and are connected to one another so that they are inverted or oriented relative to one another in opposite directions. For example, the upper curved portion projects towards an anterior side and the lower curved portion projects toward a posterior side. Of course, the upper and lower curved portions may be reversed in orientation such that the upper curved portion projects towards the posterior side, and the lower curved portion projects towards the anterior side.

The upper curved portion tends to provide vertical shock relief as well as protection against over extension of the knee. The lower curved portion tends to provide for flexion of the knee during stance and swing phases of a gait.

The lower curved portion defines a convex open space, wherein a damping or limiting member may be placed to damp or limit the rapid extension of the knee that results from the energy returning nature of the material of the spring member.

According to a variation of the embodiment, the knee is a spring member having only a single asymmetrically curved portion. An upper base portion is provided that extends from one end of the posterior curved portion preferably in a substantially planar configuration. A lower base portion is provided that extends from another end of the posterior curved portion preferably in a substantially planar configuration. The upper and lower base portions are spaced apart from one another and are preferably arranged generally parallel to relative to one another.

The orientation of the asymmetrically curved portion may be positioned to project in either of the anterior or posterior directions.

In another embodiment, the prosthetic joint includes an upper mount member, a lower frame member, and a spring or biasing member. The upper mount member is pivotally connected to an upper portion of the lower frame member. The biasing member has an upper end and a lower end, with the lower end connected to the lower portion of the lower frame member and the upper end connected to the upper mount member. These connections may be of any suitable type that allows compression of the biasing member, with pivotal connections being preferred so that the internal stresses of the biasing member near the connections do not become too large and so that the biasing member does not transfer a rotational moment, in the axis of the joint rotation, to the upper mount member or the lower frame member.

The pivotal connection between the upper end of the biasing member and the upper mount may be located posterior to the pivotal connection between the upper mount and the lower frame member.

The prosthetic joint is constructed so that during a stance phase, the biasing member provides stance flexion and, during a swing phase, the biasing member provides energy return.

In another embodiment of the prosthetic joint, a damper is disposed between the biasing member and the lower frame member. The damper may have a first passageway and the lower frame member may have a second passageway such that the first passageway communicates with the second passageway. Additionally, the damper may have a first end and a second end, with the second end connected to an interior surface of the lower frame member. The biasing member may have a posterior surface that contacts the first end of the damper during a swing phase of the prosthetic joint so that the first and second passageways act to slow energy return provided by the biasing member during the swing phase.

In yet another embodiment, the shape and size of the first and second passageways can be varied in order to adjust the energy return of the biasing member during the swing phase.

Another feature is that the first end of the damper can be adjusted to be closer to and further from the posterior surface of the biasing member in order to adjust the energy return of the biasing member during the swing phase.

Another feature comprises stiffness adjusting mechanisms located around an outer surface of the damper such that the stiffness of the damper may be adjusted in order to adjust the energy return of the biasing member during the swing phase.

In another embodiment, the prosthetic joint is configured to brake over a pivot point during a sitting phase.

According to this embodiment, a cushion is located near the upper portion of the lower frame member, anterior to the connection between the upper mount member and the lower frame member, such that, when the prosthetic joint is in a stance phase, the upper mount rests upon the cushion and the cushion provides stance flexion.

In yet another embodiment, along with the above described first damper, a second damper may be disposed between the biasing member and the lower frame member in order to provide resistance against the flexion of the biasing member during the toe-off phase. The second damper can be provided with stiffness adjusting mechanisms in order to adjust the amount of resistance provided against the flexion of the biasing member during the toe-off phase. The second end of the second damper can be adjusted to be closer to and further from the anterior surface of the biasing member in order to adjust the amount of resistance provided against the flexion of the biasing member during the toe-off phase.

Additionally, in other embodiments, the amount and rate of energy return during the swing phase can be varied.

The advantages of the improved energy returning prosthetic joint disclosed herein include a simpler mechanical design that is not as susceptible to failure as a more complex, polycentric design, while at the same time providing a good balance between the need for stability in the stance phase, while allowing for stance flexion, providing resistance to flexion during the toe-off phase and further providing energy return assistance during the swing phase.

These, and other advantages of the improved energy returning prosthetic joint, will become better understood in light of the following description, appended claims, and accompanying drawings.

BRIEF DESCRIPTION OF THE DRAWINGS

FIG. 10 is a side elevational view of a third embodiment of an energy returning prosthetic joint, shown in a full extension position.

FIG. 11 is a side elevational view of the energy returning prosthetic joint in FIG. 10, shown in an intermediate flexion position.

FIG. 12 is a side elevational view of the energy returning prosthetic joint in FIG. 10, shown in a maximal flexion position.

DETAILED DESCRIPTION OF VARIOUS EMBODIMENTS

Figures 1, 2:
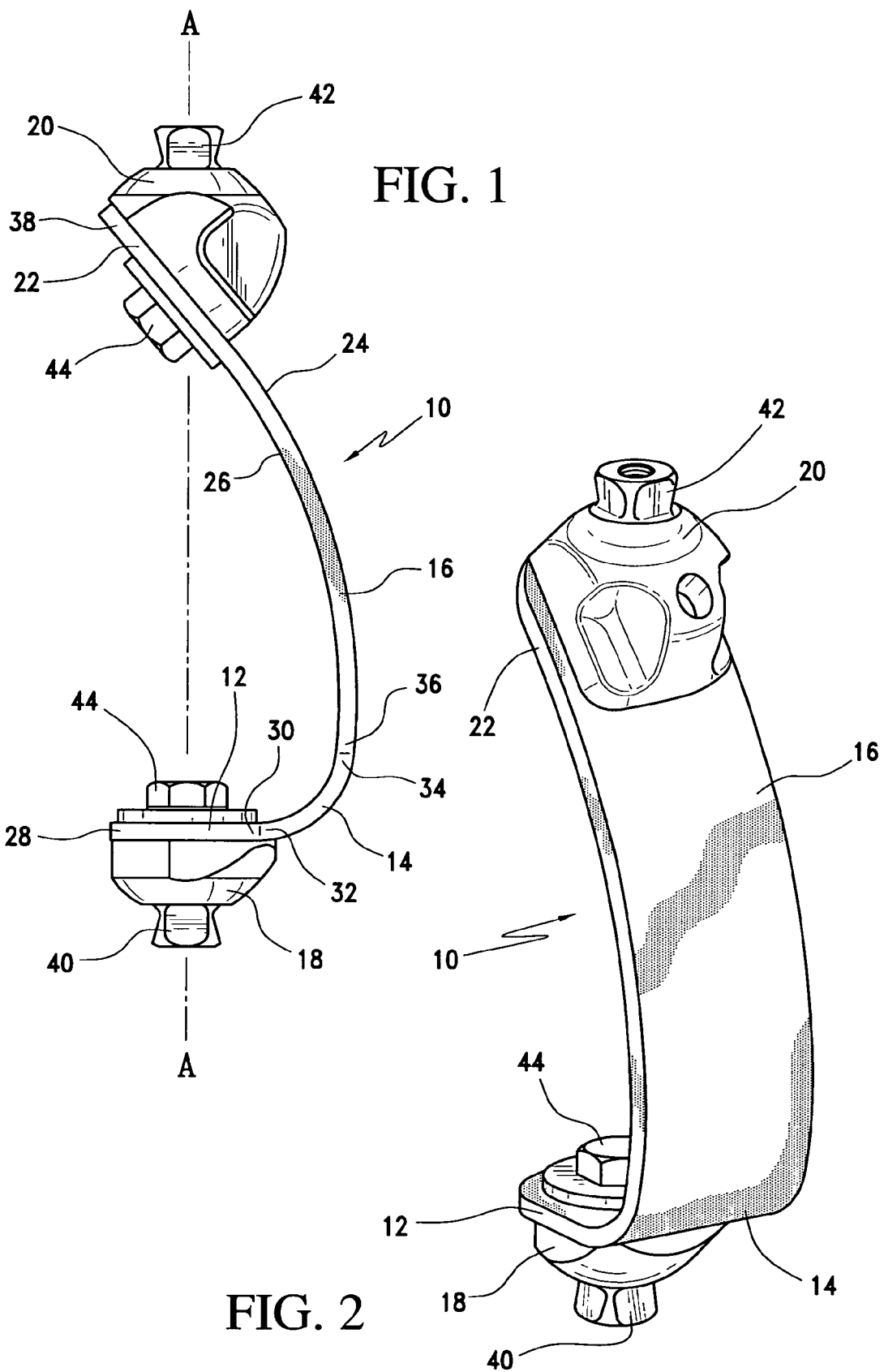
FIG. 1 is a side elevational view of one embodiment of an energy returning prosthetic joint.
FIG. 2 is a perspective view of the prosthetic joint according to FIG. 1.

A. Environment and Context of the Various Embodiments

In order to understand the operation of the energy returning prosthetic joint described herein, a basic discussion of the gait cycle is required. A gait cycle defines the movement of the leg between successive heel contacts of the same foot. The gait cycle has two phases: stance and swing. The stance phase has three time periods: heel-strike, mid-stance and toe-off.

At some point during mid-stance, the knee joint will be at full extension. An actual knee joint will have some flexion between heel-strike and mid-stance and between mid-stance and toe-off. This is called "stance flexion." Not all prosthetic joints provide for stance flexion, and for those that do, they are either mechanically complex, expensive, or both. Moreover, these prosthetic joints typically require frequent maintenance and replacement. Additionally, the amount of stance flexion required can vary from user to user, while most prosthetic joints have no adjustability.

Maximum flexion of the knee joint, while walking, will occur at the end of the toe-off phase. The amount of maximum flexion is typically determined in pan by the speed at which a person is walking. The faster a person walks, the greater the amount of maximum flexion, while the slower a person walks, the lesser the amount of maximum flexion. In a natural knee, the amount of maximum flexion can be controlled and limited via the musculature of the leg. In a prosthetic knee joint, some artificial means of controlling and limiting the amount of maximum flexion must be provided. Immediately following the end of the toe-off phase begins the swing phase.

While the stance phase has three time periods, the swing phase has two time periods: acceleration and deceleration. The acceleration phase begins immediately following the maximum flexion during the toe-off phase. During the acceleration phase, the lower portion of the leg, consisting of the shin and foot, begins to swing back towards full extension. In a natural knee joint, a deceleration phase follows the acceleration phase, during which the lower portion of the leg continues to swing towards full extension. Some prosthetic joints do not provide for any deceleration during the swing phase. Other prosthetic joints provide deceleration by using costly and bulky hydraulic or pneumatic cylinders. The amount of deceleration required can vary from user to user, while most prosthetic joints have no adjustability.

In one embodiment of the invention, the energy returning prosthetic joint described herein provides both stance flexion during the stance phase, and deceleration during the swing phase. In another embodiment of the invention, the energy returning prosthetic joint described herein also provides a limitation on the maximum amount of flexion during the toe-off phase. The embodiments described herein accomplish these features with a mechanically simple construction, without complex linkages subject to frequent maintenance and replacement.

For further ease of understanding the joint disclosed herein, a description of a few terms is necessary. As used herein, the term "upper" has its ordinary meaning and refers to a location that is above, or higher than another location. Likewise, the term "lower" has its ordinary meaning and refers to a location that is below, or underneath another location. The term "posterior" also has its ordinary meaning and refers to a location that is behind or to the rear of another location. Lastly, the term "anterior" has its ordinary meaning and refers to a location that is ahead or to the front of another location.

B. First Embodiment

A first embodiment of an energy returning prosthetic joint is illustrated in FIGS. 1 and 2. In accordance with this embodiment, a prosthetic joint 10 is constructed from a material having an energy returning property. The knee has a base portion 12 configured in a substantially planar shape, and has first and second ends 28, 30. An arcuate portion 14 having a first end 32 is connected to the second end 30 of the base portion. A first end portion 36 of an asymmetrical curvilinear portion 16 is connected to a second end 34 of the arcuate portion 14. Preferably, the curvilinear portion 16 extends from the arcuate portion 14 obliquely over and relative to the base portion 12.

The curvilinear portion 16 has a variable radius such that its curvature varies over its length. For example, according to the embodiment shown in FIG. 1, the curvature of the curvilinear portion 16 preferably has a greater curvature near its first end portion 36. The curvature greatly decreases to nearly or at a straight portion 22 near a second end portion 38 of the curvilinear portion 16.

In order to couple upper and lower leg prostheses, the prosthetic joint 10 is provided with first and second attachment members 18, 20 that are secured to portions of the prosthetic joint. Preferably, the first attachment member 18 is secured onto the base portion 12 and the second attachment member 20 is secured onto the curvilinear portion 16. The attachment members 18, 20 are secured onto a first side 24 of the prosthetic joint and are preferably secured to the prosthetic joint 10 with fasteners 44 that extend into the attachment members 18, 20 from a second side 26 of the prosthetic joint 10.

Each of the attachment members includes a locking feature 40, 42 that is provided for coupling the upper and lower portions of the prosthetic leg. The locking features 40, 42 of the attachment members 18, 20 are axially aligned with one another along axis A-A in a static configuration so as to provide stability and balance of the knee.

Since the curvilinear portion 16 extends obliquely relative to the base portion 12, the second attachment member 20 is shaped differently from the first attachment member 18 such that the second attachment member 20 is flush with the straight portion 22 while maintaining alignment of the locking feature 42 with the locking feature 40 of the first attachment member.

Despite the arcuate portion 14 being shown in FIG. 1 as having a generally uniform radius, it will be understood that the arcuate portion 14 may have a variable radius, thereby defining a non-uniform shape. While shown as being asymmetric, the curvilinear portion 16 may be constructed so that it is symmetric or substantially symmetric according to the desired energy returning properties of the prosthetic joint and the patient.

The orientation of the asymmetrical curvilinear portion may be positioned to project in either of the anterior or posterior directions.

C. Second Embodiment

Figure 3:
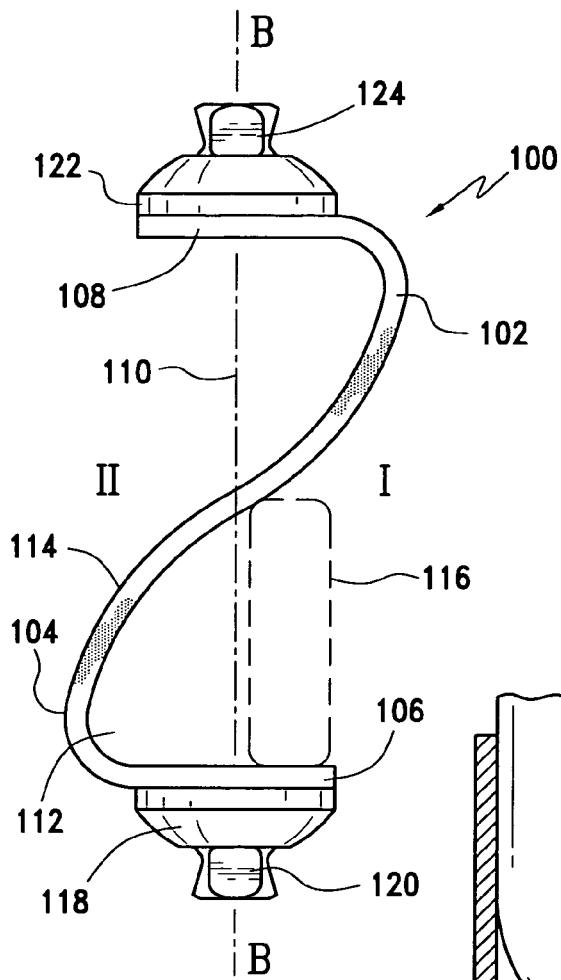
FIG. 3 is a side elevational view of another embodiment of an energy returning prosthetic joint.

In accordance with another embodiment of the prosthetic joint, FIG. 3 illustrates an energy returning prosthetic joint 100 comprising a generally "S" shaped spring member vertically oriented between the upper, portion, or socket, of a leg prosthesis and the lower portion, or pylon, of the leg prosthesis. An example of upper and lower portions of a leg prosthesis system is described in U.S. Pat. No. 6,589,289 incorporated herein by reference.

In accordance with the illustration shown in FIG. 3, the anterior side of the knee is represented by I and the posterior side of the knee is represented by II. The axis B-B demarcates the boundary between the anterior and posterior sides of the knee 100.

The general "S" curve of the knee 100 defines an upper, anterior curved portion 102, joined to a lower, posterior curved portion 104. The anterior curved portion 102 terminates, at the top of the knee 100, with an upper arm 108 that is adapted for attachment to the upper portion of a leg prosthesis or to an attachment member 122 having a locking feature 124 for attachment to the upper portion of a leg prosthesis. Similarly, the posterior curved portion 104 terminates, at the bottom of the knee 100, with a lower arm 106 that is adapted for attachment to the lower portion of a leg prosthesis or to an attachment member 118 having a locking feature 120 for attachment to the lower portion of a leg prosthesis.

Preferably, the upper and lower arms 108, 106 are generally planar so that the attachment members 118, 122 are mounted flush with the upper and lower arms 108, 106. While not shown, the attachment members 118, 122 may be mounted to the knee 100 with any known and suitable fasteners, for example the fasteners 44 shown in the embodiment of FIG. 1. As with the embodiment of FIG. 1, the locking features 120, 124 corresponding to the attachment members 118, 124 are preferably aligned along a common axis, axis B-B.

The anterior curved portion 102 defines a convex anterior open space 110, while the posterior curved portion 104 defines a convex anterior open space 126. The knee 100 is formed of an energy returning material such as certain plastics or certain composite materials including carbon or aramid fibers. The energy returning material may also be reinforced with memory shape alloys, or other suitable metal components.

The anterior curved portion 102 may be made relatively stiff in comparison with the remainder of the knee 100, such as by varying the thickness, width, or material composition in the region of the anterior curved portion 102. Increased stiffness of the anterior curved portion 102 assists to restrict the knee 100 from over-extension, while the anterior curved portion 102 is still allowed some flexion to provide for vertical shock relief as the anterior curved portion 102 compresses somewhat under weight during the stance portion of the gait.

The posterior curved portion 104 allows for flexion, by opening of the posterior curved portion 104 during knee flexion periods of the gait stance and swing. A damping or limiting member 116 may be disposed within the convex anterior open space 112 of the knee 100 in order to control or limit the rapid extension of the knee 100 resulting from the energy returning nature of the material of the knee 100. The damping or limiting member 116 may be, for example, a polymer rod or post that prevents excessive closure of the posterior curved portion 104 that might result from rapid or over extension of the knee 100.

In certain embodiments, the damping or limiting member 116 may be pre-tensioned to enhance performance in a preferred direction. The damping or limiting member 116 performs a limiting function if it is made of a rigid material, while if the damping or limiting member 116 is made of a deformable resilient material it performs a damping function as the material compresses, as well as a limiting function once the material reaches a deformable limit.

Figure 4:
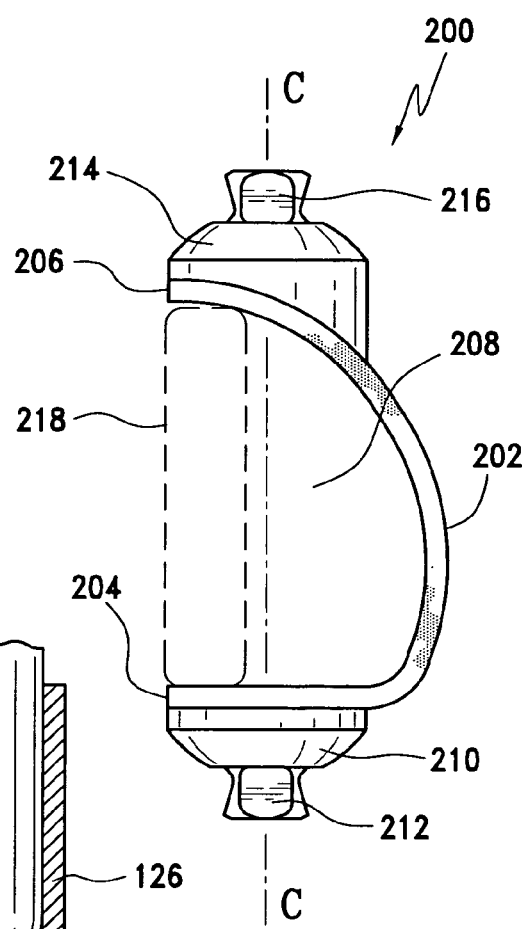
FIG. 4 is a side elevational view of yet another embodiment of an energy returning prosthetic joint.

Turning now to FIG. 4, a variation of the embodiment of FIG. 3 is illustrated wherein an energy returning prosthetic joint 200 comprises a generally "C" shaped spring member disposed between the upper portion of a leg prosthesis and the lower portion of the leg prosthesis.

The "C" shape of the knee 200 defines a single asymmetrically curved portion 202, which defines a convex open space 208. The curved portion 202 terminates at the top of the knee 200 with an upper arm 206 that is adapted for attachment to the upper portion of a leg prosthesis or to an attachment member 214 having a locking feature 216 for attachment to the upper portion of a leg prosthesis. Similarly, the curved portion 202 terminates, at the bottom of the knee 200, with a lower arm 204 that is adapted for attachment to the lower portion of a leg prosthesis or to an attachment member 210 having a locking feature 212 for attachment to the lower portion of a leg prosthesis.

The knee 200 allows for flexion, by opening of the curved portion 202 during knee flexion periods of the gait stance. As described in the previous embodiment, a damping or limiting member 218 may be disposed within the convex anterior open space 208 to control or limit the rapid extension of the knee 200 resulting from the energy returning nature of the material thereof.

Figure 5:
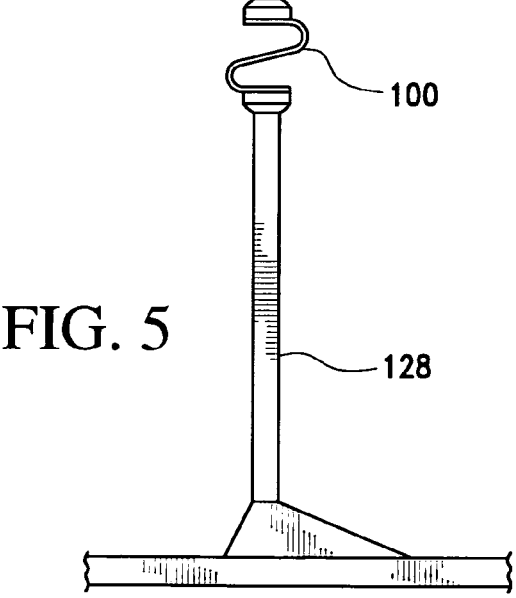
FIG. 5 is a side elevational view of a prosthetic assembly incorporating a prosthetic joint.

Referring to FIG. 5, an exemplary energy returning prosthetic joint 100 is shown coupling an upper portion 126 of a leg prostheses, the upper portion 126 comprising a hard socket, to a lower portion 128 of the leg prostheses, the lower portion 128 comprising a pylon and a foot.

Because gait is asymmetrical with regards to flexion and extension, the spring cannot be perfectly shaped in the S and C shapes described in some of the embodiments. As a result, the energy returning knee must be tuned to accommodate response of the knee and preferably is asymmetrical. Such tuning may include providing different radii to portions of the spring member, using different material thicknesses, and inserting different types of fibers into a laminate used to construct the knee.

Numerous materials and composites may be employed to construct the energy returning knee according to the invention. Some of the materials that may be used include carbon fiber, glass fiber, titanium, stainless steel, resins, and epoxies. Memory alloys may also be considered. Of particular note, if a laminate is used to construct the knee, such as carbon fiber, different types of fibers and layers may be incorporated, such as glass or titanium fibers, at critical points in the curvature of the spring member.

It will be understood that the prosthetic joint of the second embodiment in FIG. 3 may be reversed in orientation, such that "I" may denote the posterior side, and "II" may denote the anterior side. Also, the variation of FIG. 4 may be similarly reversed so that the curved portion projects either toward the anterior or posterior sides.

D. Third Embodiment

Figure 6:
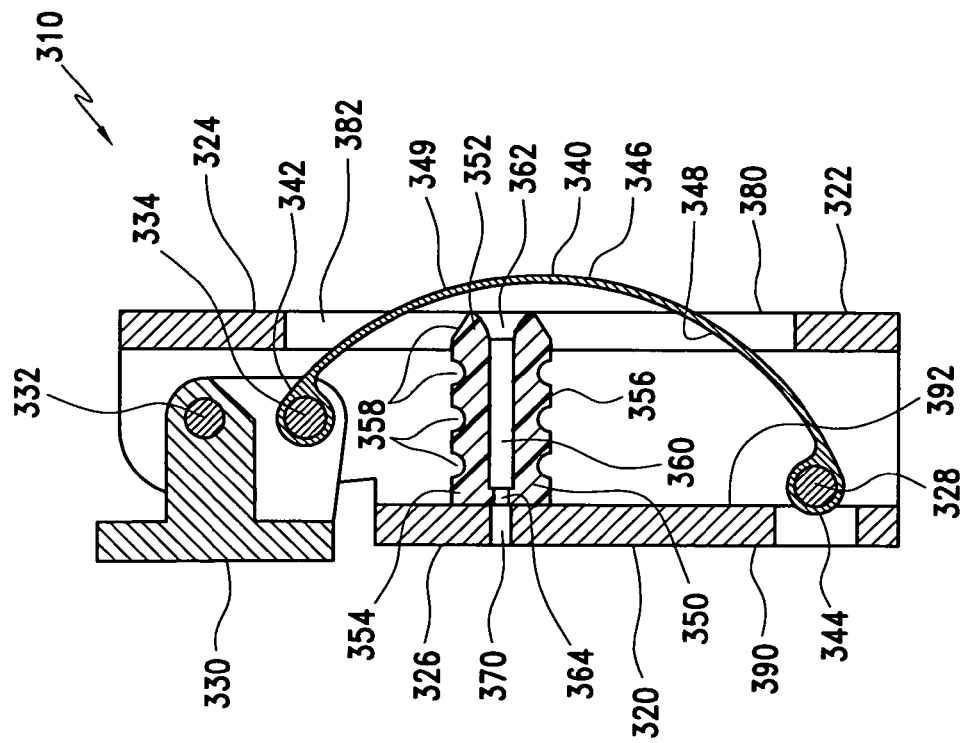
FIG. 6 is a side elevational view of another embodiment of an energy returning prosthetic joint, shown in a full extension position.
Figure 7:
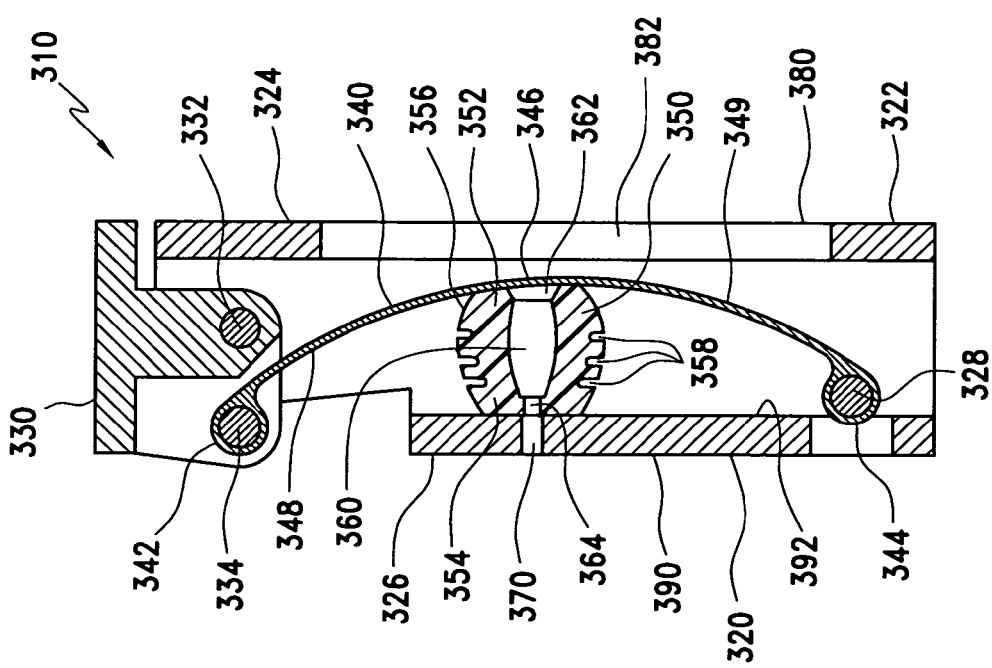
FIG. 7 is a side elevational view of the energy returning prosthetic joint in FIG. 6, shown in a maximal flexion position.

Another embodiment of an energy returning prosthetic joint is illustrated in FIGS. 6 and 7. In accordance with this embodiment, the joint 310 has a lower frame member 320 constructed from an appropriate material such as those capable of providing lightweight structural support. Examples of such materials include, but are not limited to, plastics, steel alloys, aluminum alloys, other metals, ceramics, or other rigid materials. The lower frame member has a posterior surface 390, an interior surface 392, and an anterior surface 380. The lower frame member also has a lower portion 322, an upper portion 324, and a middle portion 326.

An upper mount member 330 is connected to the upper portion 324 of the lower frame member 320. The upper mount member 330 is constructed of any suitable material such as those capable of providing lightweight structural support. Examples of such materials include, but are not limited to, plastics, steel alloys, aluminum alloys, other metals, ceramics, or other rigid materials. The connection between the upper mount member 330 and the upper portion 324 of the lower frame member 320 is a first pivot connection 332.

The joint 310 is mounted to a prosthetic member in any conventional manner, such as by providing four threaded holes in the lower frame member 320 and the upper mount member 330 that will fit any standard prosthetic component. The prosthetic components allow the joint 310 to be attached to upper and lower prosthetic members (not illustrated).

Connected to the upper mount member 330 and the lower frame member 320 is a spring or biasing member 340. The biasing member 340 can be made from any suitable lightweight material that can provide the appropriate biasing forces, such as metals and synthetic or composite materials. The materials selected for the biasing member 340 should allow for bending of the biasing member 340 without permanent deformation of the biasing member 340.

Another factor in determining the appropriate material to be used for the biasing member 340 is that the modulus of the material should be selected to match the weight of the user and the desired range of motion of the joint 310. Examples of appropriate materials include, but are not limited to, spring steels, carbon or glass fibers in resins, or specially treated plastics. To further control the spring response, a polymer dampening material may be adhered to the biasing member 340. According to one variation, the biasing member 340 is a carbon fiber spring or member.

The biasing member 340 has an upper end 342, a lower end 344, a middle portion 346, a posterior surface 348 and an anterior surface 349, and can be constructed as a leaf spring, or any other suitable shape that provides the appropriate biasing forces. The biasing member 340 could be, for example, formed in an "S" shape in order to yield different response curves. The bending of an "S" shaped biasing member 340 would require much less horizontal displacement than, for example, a "C" shaped biasing member 340 for the same amount of vertical displacement. The illustrated biasing member 340 is formed as a leaf type spring and should be pre-bent to control which direction the biasing member 340 will bend.

The upper end 342 of the biasing member 340 is connected to the upper mount member 330 at a second pivot connection 334. The second pivot connection 334 is located posterior to the first pivot connection 332. The lower end 344 of the biasing member 340 is connected to the lower frame member 320 at a third pivot connection 328. The pivot connection can be constructed in any appropriate manner including, but not limited to, laminating the eye, bending the biasing member 340 around the eye, clamping the biasing member 340 to the eye, or providing a rubber bushing vulcanized to the end of the biasing member 340.

Further, the second pivot connection 334 could be replaced with any appropriate connection including, but not limited to, providing a spiral end at the upper end 342 of the biasing member 340. Additionally, the third pivot connection 328 can be replaced with any appropriate connection including, but not limited to, a rigid connection.

The energy returning prosthetic joint 310 also includes a damper 350 connected to the lower frame member 320 in any suitable fashion, such as by bonding or mechanical fastening. The damper 350 can be made of any suitable material that can absorb energy, for example rubber, plastic or a synthetic material such as a polymer. The damper 350 has a first end 352, a second end 354 and an outer surface 356. The second end 354 of the damper 350 is connected to the interior surface 392 at the middle portion 326 of the lower frame member 320 in any conventional manner.

The damper 350 further includes a first opening 362 in the first end 352, a second opening 364 in the second end 354 and a first passageway 360 that extends through the damper 350 from the first opening 362 to the second opening 364. The sizes and shapes of the first opening 362, second opening 364 and first passageway 360 can be adjusted to change the volume of the damper 350, and hence the stiffness of the damper 350. The sizes and shapes of the first opening 362, second opening 364 and first passageway 360 can also be adjusted to limit the amount of airflow through the openings and the passageway, as will be described in further detail below.

The damper 350 also includes stiffness adjusting mechanisms 358 located along the outer surface 356 of the damper 350. The stiffness adjusting mechanisms 358 can consist of any structure that changes the volume and/or the geometry of the damper 350, such as grooves having any desired shape, notches and tapers.

The lower frame member 320 additionally includes a second passageway 370, located in the middle portion 326 of the lower frame member 320. The second passageway 370 extends between the posterior surface 390 of the lower frame member 320 and the interior surface 392 of the lower frame member 320, and is in communication with the second opening 364 in the damper 350. This communication allows the passage of air from the first end 352 of the damper 350, through the first opening 362, through first passageway 360, through the second opening 364, through the second passageway 370 to the environment past the posterior surface 390 of the lower frame member. The size and shape of the second passageway 370 can be varied in order to adjust the amount of airflow therethrough. The two passageways 360, 370, and the first and second openings 362, 364 form an air vent that can be used to adjust the energy return of the biasing member 340, as will be further discussed below.

In this particular embodiment the anterior surface 380 of the lower frame member 320 includes a clearance opening 382 that allows the biasing member 340, while in a flexed position, to extend through the anterior surface 380 of the lower frame member 320, as can be seen in FIG. 7.

In another variation, not shown, the anterior surface 380 of the lower frame member 320 may not have the clearance opening 382, but may be located such that when the biasing member 340 is in a maximally flexed state, the anterior surface 349 of the biasing member 340 does not contact the lower frame member 320.

In operation, the joint 310 may be used as a knee joint. The joint 310 is shown in full extension in FIG. 6, with the biasing member 340 minimally flexed and the damper 350 compressed. The biasing member 340 provides the user with stance flexion during the stance phase via the flexion of the biasing member 340. Additionally, the posterior surface 348 of the biasing member 340 forms an air tight seal with the first end 352 of the damper 350. During the end of the mid-stance phase and the beginning of the toe-off phase, the biasing member 340 will flex and the damper 350 will expand.

The rate of this flexion and expansion is governed by the fact that air is sucked through the second passageway 370, through the second opening 364 and into the first passageway 360. The sizes of the second passageway 370, through the second opening 364 and into the first passageway 360 can all be varied to adjust the rate of release of the biasing member 340 from the damper 350. Additionally the location of the first end 352 of the damper 350 can be varied in relation to the posterior surface 348 of the biasing member 340 in order to allow for another adjusting parameter for the rate of release.

The joint 310 is shown in maximum flexion in FIG. 7. This position may occur while a user is seated, and is used in an exemplary way to show that during the maximal flexion of the joint 310 during the toe-off phase, the biasing member 340 no longer forms an airtight seal with the first end 352 of the damper 350. During the acceleration period of the swing phase, the biasing member 340 provides energy return to the lower flame member 320. At a point prior to full extension, the posterior surface 348 of the biasing member 340 will contact the first end 352 of the damper 350.

Both the stiffness of the damping member 350 and the forcing of air through the passageways 360, 370 and the second opening 364 provide the damping which slows the energy return of the biasing member 340. As discussed previously, the stiffness adjusting mechanisms 358, the sizes and shapes of the openings 362, 364 and passageways 360, 370, and the location of the first end 352 of the damper 350, can all be varied in order to adjust the energy return of the biasing member 340, in order to provide appropriate deceleration during the swing phase. This allows the joint 310 to be adjustable to different user's gait dynamics.

E. Fourth Embodiment

Figure 9:
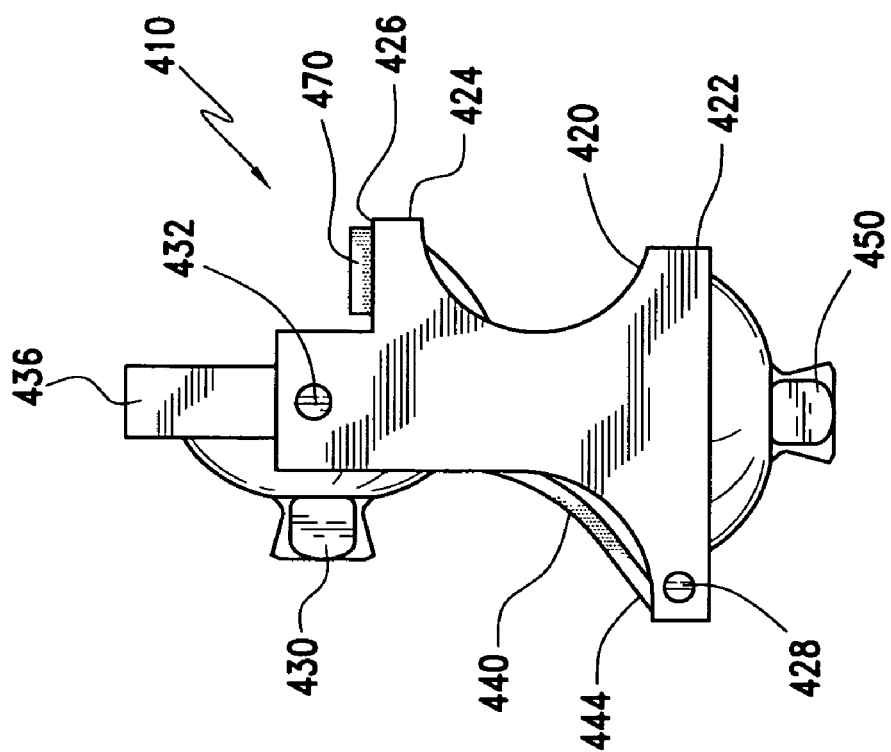
FIG. 9 is a side elevational view of the energy returning prosthetic joint in FIG. 8, shown in a maximal flexion position.
Figure 8:
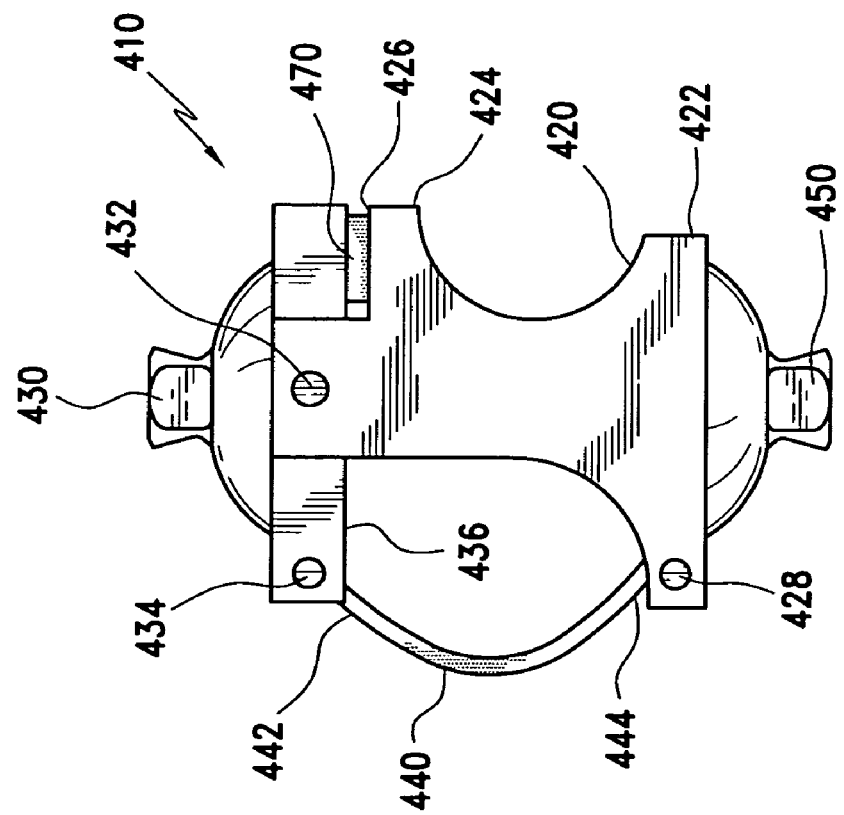
FIG. 8 is a side elevational view of a second embodiment of an energy returning prosthetic joint, shown in a full extension position.

A second embodiment of an energy returning prosthetic joint is illustrated in FIGS. 8 and 9. In accordance with this embodiment, the joint 410 has a lower frame member 420 constructed from an appropriate material such as one capable of providing lightweight structural support, such as the materials discussed above in section D. The lower frame member has a lower portion 422, an upper portion 424, and a mounting surface 426 for a damper or cushion 470. The lower frame member can be formed integrally with a U-shape defined by two flange portions that extend from a base towards an upper mount member 430. Alternatively, the lower frame member 420 can be formed from components, including a lower mount member 450, and assembled in a conventional way, such as by bonding or with mechanical fasteners. The preferred design would provide a yoke that allows the upper mount member 430 to rotate at least 90 degrees.

In a one embodiment, the mounting surface 426 would bridge the yoke portion of the lower frame member 420 in order to provide more rigidity to the joint 410.

The upper mount member 430 is connected to the upper portion 424 of the lower frame member 420. The upper mount member 430 is constructed of any suitable material such as those capable of providing lightweight structural support, such as the materials discussed above in section D. The connection between the upper mount member 430 and the upper portion 424 of the lower frame member 420 is a first pivot connection 432 that allows the upper mount member 430 to rotate at least 90 degrees. The upper mount member 430 also has a lower surface 436. The cushion 470 is positioned anterior to the first pivot connection 432 such that the anterior portion of the lower surface 436 of the upper mount member 430 can rest upon the cushion 470 during fill extension.

Connected to the upper mount member 430 and the lower frame member 420 is a spring or biasing member 440. The biasing member 440 can be made from any material that can provide the appropriate biasing forces, such as the materials discussed above in section D. According to one variation, the biasing member 440 is a carbon fiber spring or member. The biasing member 440 has an upper end 442, a lower end 444, and can be constructed as a leaf spring, or any other suitable shape that provides the appropriate biasing forces, such as those discussed above in section D. The upper end 442 of the biasing member 440 is connected to the upper mount member 430 at a second pivot connection 434. The second pivot connection 434 is located posterior to the first pivot connection 432. The lower end 444 of the biasing member 440 is connected to the lower frame member 420 at a third pivot connection 428. The second and third pivot connections 434, 428 may be replaced with any appropriate connection, as discussed above in section D.

In operation, the joint 410 may be used as a knee joint. The joint 410 may be connected to a prosthetic leg (not shown) in any conventional manner including, but not limited to, the standard pyramid attachment system. The joint 410 is shown in full extension in FIG. 8 with the lower surface 436 of the upper mount member 430 resting on the cushion 470. The cushion 470 provides stance flexion during the stance phase. The cushion 470 can vary in size and shape, and can contact the lower surface 436 across the entire width, or merely a portion thereof, of the upper mount member 430. Any suitable arrangement can be used in order to provide the appropriate amount of stance flexion for each individual user.

The joint 410 is shown in maximum flexion in FIG. 9. This position may occur while a user is seated. In order for a user to go from a standing position to a seated position, the user must brake the biasing member 440 over a pivot point. In other words, at some point during the rotation of the upper mount member 430 from the full extension position shown in FIG. 8 to the maximal flexion position shown in FIG. 9, just after the resistance of the biasing member 440 is at a maximum, the biasing member 440 will invert.

The inversion of the biasing member 440 changes how the biasing member 440 biases the joint 410. In FIG. 8, the biasing member 440 biases the joint 410 into the full extension position. In FIG. 9, the biasing member 440 biases the joint 410 into the maximal flexion position. This relationship effectively provides a locking mechanism that is relatively easy to overcome. This relationship generally locks the joint 410 into one of two positions, but allows for flexion in both of the positions.

F. Fifth Embodiment

A fifth embodiment of an energy returning prosthetic joint is illustrated in FIGS. 10, 11 and 12. In accordance with this embodiment, the joint 510 is constructed very similarly to the first embodiment. The joint 510 has a lower frame member 520 constructed from an appropriate material such as those capable of providing lightweight structural support. Examples of such materials include, but are not limited to, plastics, steel alloys, aluminum alloys, other metals, ceramics, or other rigid materials. The lower frame member 520 has a posterior surface 590, a first interior surface 592, a second interior surface 594, and an anterior surface 580. The lower frame member 520 also has a lower portion 522, an upper portion 524, and a middle portion 526.

An upper mount member 530 is connected to the upper portion 524 of the lower frame member 520. The upper mount member 530 is constructed of any suitable material such as those capable of providing lightweight structural support. Examples of such materials include, but are not limited to, plastics, steel alloys, aluminum alloys, other metals, ceramics, or other rigid materials. The connection between the upper mount member 530 and the upper portion 524 of the lower frame member 520 is a first pivot connection 532.

The joint 510 is mounted to a prosthetic member in any conventional manner, such as by providing four threaded holes in the lower frame member 520 and the upper mount member 530 that will fit any standard prosthetic component. The prosthetic components allow the joint 510 to be attached to upper and lower prosthetic members (not illustrated).

Connected to the upper mount member 530 and the lower frame member 520 is a spring or biasing member 540. The biasing member 540 can be made from any suitable lightweight material that can provide the appropriate biasing forces, such as metals and synthetic or composite materials. The materials selected for the biasing member 540 should allow for bending of the biasing member 540 without permanent deformation of the biasing member 540. Another factor in determining the appropriate material to be used for the biasing member 540 is that the modulus of the material should be selected to match the weight of the user and the desired range of motion of the joint 510. Examples of appropriate materials include, but are not limited to, spring steels, carbon or glass fibers in resins, or specially treated plastics. To further control the spring response, a polymer dampening material may be adhered to the biasing member 540. According to one variation, the biasing member 540 is a carbon fiber spring or member.

The biasing member 540 has an upper end 542, a lower end 544, a middle portion 546, a posterior surface 548 and an anterior surface 549, and can be constructed as a leaf spring, or any other suitable shape that provides the appropriate biasing forces. The biasing member 540 could be, for example, formed in an "S" shape in order to yield different response curves. The bending of an "S" shaped biasing member 540 would require much less horizontal displacement than, for example, a "C" shaped biasing member 540 for the same amount of vertical displacement. The illustrated biasing member 540 is formed as a leaf type spring and should be pre-bent to control which direction the biasing member 540 will bend.

The upper end 542 of the biasing member 540 is connected to the upper mount member 530 at a second pivot connection 534. The second pivot connection 534 is located posterior to the first pivot connection 532. The lower end 544 of the biasing member 540 is connected to the lower frame member 520 at a third pivot connection 528. The pivot connection can be constructed in any appropriate manner including, but not limited to, laminating the eye, bending the biasing member 540 around the eye, clamping the biasing member 540 to the eye, or providing a rubber bushing vulcanized to the end of the biasing member 540.

Further, the second pivot connection 534 could be replaced with any appropriate connection including, but not limited to, providing a spiral end at the upper end 542 of the biasing member 540. Additionally, the third pivot connection 528 can be replaced with any appropriate connection including, but not limited to, a rigid connection.

The energy returning prosthetic joint 510 also includes a first damper 550 connected to the lower frame member 520 in any suitable fashion, such as by bonding or mechanical fastening. The first damper 550 can be made of any suitable material that can absorb energy, for example a synthetic material such as a polymer. The first damper 550 has a first end 552, a second end 554 and an outer surface 556. The second end 554 of the first damper 550 is connected to the first interior surface 592 at the middle portion 526 of the lower frame member 520, in any conventional manner.

The first damper 550 further includes a first opening 562 in the first end 552, a second opening 564 in the second end 554 and a first passageway 560 that extends through the first damper 550 from the first opening 562 to the second opening 564. The sizes and shapes of the first opening 262, second opening 564 and first passageway 560 can be adjusted to change the volume of the first damper 550, and hence the stiffness of the first damper 550. The sizes and shapes of the first opening 562, second opening 564 and first passageway 560 can also be adjusted to limit the amount of airflow through the openings and the passageway, as will be described in further detail below.

The first damper 550 also includes stiffness adjusting mechanisms 258 located along the outer surface 556 of the first damper 550. The stiffness adjusting mechanisms 558 can consist of any structure that changes the volume and/or the geometry of the first damper 550, such as grooves having any shape, notches and tapers.

The lower frame member 520 additionally includes a second passageway 570, located in the middle portion 226 of the lower frame member 520. The second passageway 570 extends between the posterior surface 590 of the lower frame member 520 and the first interior surface 592 of the lower frame member 520, and is in communication with the second opening 564 in the first damper 550. This communication allows the passage of air from the first end 552 of the first damper 550, through the first opening 562, through first passageway 560, through the second opening 564, through the second passageway 570 to the environment past the posterior surface 590 of the lower frame member. The size and shape of the second passageway 570 can be varied in order to adjust the amount of airflow therethrough. The two passageways 560, 570, and the first and second openings 562, 564 form an air vent that can be used to adjust the energy return of the biasing member 540, as discussed above in section D.

Additionally the location of the first end 552 of the first damper 550 can be varied in relation to the posterior surface 548 of the biasing member 540 in order to allow for adjusting the rate of release of the biasing member 540 from contact with the first end 552 of the first damper 550.

Further, in this embodiment the anterior surface 580 of the lower frame member 520 includes a clearance opening 582 that may allow the biasing member 540, while in a flexed position, to extend through the anterior surface 580 of the lower frame member 520, as can be seen in FIG. 12.

In another variation, not shown, the anterior surface 580 of the lower frame member 520 may not have the clearance opening 582, but may be located such that when the biasing member 540 is in a maximally flexed state, the anterior surface 549 of the biasing member 540 does not contact the lower frame member 520.

In addition to the clearance opening 582, the lower frame member 520 includes a second damper 550 disposed on the second interior surface 594 of the lower frame member 520. The second damper 550 has a first end 552, a second end 554, and an outer surface 556. The second damper 550 may be connected to the second interior surface 594 of the lower frame member 520 in any conventional manner or, as illustrated, the second damper may have a connection post 564 formed at the first end 552 of the second damper 550. The second damper 550 may be constructed in a similar manner as the first damper 550, including a passageway and an opening through the first end 554, and a passageway through the lower portion 522 of the lower frame member 520. Further, the second damper 550 can be made of any suitable material that can absorb energy, for example rubber, plastic or a synthetic material such as a polymer.

The second damper 550 includes stiffness adjusting mechanisms 558, as described above in section D, located on the outer surface 556 of the second damper 550. The second damper 550 further includes an opening 562 in the second end 554 of the second damper 550, and a passageway or hollow portion 560, partially defined by the opening 562. This structure allows the volume, and hence the stiffness, of the second damper 550 to be adjusted.

In operation, the joint 510 may be used as a knee joint. The joint 210 is shown in full extension in FIG. 10, with the biasing member 540 minimally flexed and the first damper 550 compressed. The interaction of the biasing member 540 and the first damper 550 of the joint 510 functions in the same way as described above in section B in reference to the third embodiment of the joint 310.

In FIG. 11, the joint 510 is shown in flexion of about 60 degrees. This position of the joint 510 may occur during the toe-off phase. It can be seen that the anterior surface 549 of the biasing member 540 is in contact with the second end 554 of the second damper 550. In this manner the second damper 550 provides resistance to the flexion of the biasing member 540 in order to prevent too much flexion of the joint 510 during the toe-off phase. As previously discussed, the volume, and hence the stiffness of the second damper 550 can be adjusted in order to control the amount of resistance the second damper 550 will provide to the flexion of the biasing member 540.

The joint 510 is shown in maximum flexion of 90 degrees in FIG. 12. This position may occur while a user is seated, and is used in an exemplary way to show that during the maximal flexion of the joint 510, the biasing member 540 no longer forms an airtight seal with the first end 552 of the first damper 550. Instead, the anterior surface 549 of the biasing member 540 is in contact with the second end 554 of the second damper 550. As previously discussed, the second damper 550 acts as a cushion and provides resistance to the flexion of the biasing member 540 during the toe-off phase, or as illustrated in FIG. 12, at a sitting stage.

Further, as illustrated, the anterior surface 549 of the biasing member 540 is in contact with the second end 554 of the second damper 550 between the angles of 60 degrees and 90 degrees during flexion. Similarly to the first damper 550, the location of the second end 554 of the second damper 550, can be varied in order to adjust the amount of resistance provided against the flexion of the biasing member 540, and to vary the angles that the biasing member 540 engages the second damper 550. All of the aforementioned adjusting mechanisms allow the joint 510 to be adjustable to different user's gait dynamics.

G. Alternate Embodiments

The energy returning prosthetic joint described in the three exemplary embodiments herein is not limited to the specific structures and components described, but is merely illustrative in nature. As previously mentioned, numerous materials may be used in the construction of the energy returning prosthetic joint, including, but not limited to, carbon fiber, glass fiber, titanium, stainless steel, aluminum alloys, resins, and epoxies.

The orientation of the joints may be reversed, as in the embodiment of FIGS. 3 and 4, wherein the described anterior side may be reversed to define the posterior side, and the described posterior side would therefore be reversed to denote the anterior side.

Numerous modifications to the disclosed embodiments may occur to those skilled in the art. Such modifications are meant to be included by this disclosure, and the only limitations meant to be included are those contained in the appended claims.

We claim:

1. An energy returning prosthetic joint, comprising:
   a lower frame member having a lower portion and an upper portion;
   an upper mount member pivotally connected to the upper portion of the lower frame member;
   a biasing member having an upper end and a lower end, the lower end of the biasing member connected to the lower portion of the lower frame member and the upper end of the biasing member connected to the upper mount member; and
   a damper disposed between the biasing member and the lower frame member;
   wherein during a stance phase, the damper and the biasing member are arranged to provide stance flexion and, during a swing phase, the biasing member is arranged to provide energy return.

2. The prosthetic joint according to claim 1, wherein the lower end of the biasing member is pivotally connected to the lower portion of the lower frame member and the upper end of the biasing member is pivotally connected to the upper mount member.

3. The prosthetic joint according to claim 2, wherein the pivotal connection between the upper end of the biasing member and the upper mount is located posterior to the pivotal connection between the upper mount and the lower frame member.

4. The prosthetic joint according to claim 1 wherein the damper defines a first passageway and the lower frame member defines a second passageway, the damper and lower frame member arranged such that the first passageway communicates with the second passageway.

5. The prosthetic joint according to claim 4, wherein the damper further comprises a first end and a second end, the second end connected to an interior surface of the lower frame member, and the biasing member further including a posterior surface that contacts the first end of the damper during a swing phase of the prosthetic joint;
   whereby the first and second passageways combine to slow energy return provided by the biasing member during the swing phase.

6. The prosthetic joint according to claim 5, wherein the size of the first and second passageways are variable to adjust the energy return of the biasing member during the swing phase.

7. The prosthetic joint according to claim 5, wherein the first end of the damper is adjustably arranged closer to and further from the posterior surface of the biasing member, thereby adjusting the energy return of the biasing member during the swing phase.

8. The prosthetic joint according to claim 5, wherein the damper comprises an outer surface having stiffness adjusting mechanisms thereby adjusting energy return provided by the biasing member during a swing phase of the prosthetic joint.

9. The prosthetic joint according to claim 1, further comprising a first damper and a second damper, both disposed between the biasing member and the lower frame member.

10. The prosthetic joint according to claim 9, wherein the first damper defines a first passageway and the lower frame member defines a second passageway, the first damper and tower frame member arranged such that the first passageway communicates with the second passageway.

11. The prosthetic joint according to claim 10, wherein the first damper further comprises a first end and a second end, the second end connected to an interior surface of the lower frame member, and the biasing member further including a posterior surface that contacts the first end of the damper during a swing phase of the prosthetic joint;
   whereby the first and second passageways combine to slow energy return provided by the biasing member during the swing phase.

12. The prosthetic joint according to claim 11, wherein the size of the first and second passageways are variable to adjust the energy return of the biasing member during the swing phase.

13. The prosthetic joint according to claim 9, wherein the first end of the first damper is adjustably arranged closer to and further from the posterior surface of the biasing member, thereby adjusting the energy return of the biasing member during the swing phase.

14. The prosthetic joint according to claim 9, wherein the first damper comprises an outer surface having stiffness adjusting mechanisms thereby adjusting energy return provided by the biasing member during a swing phase of the prosthetic joint; and wherein the second damper comprises an outer surface having stiffness adjusting mechanisms, thereby adjusting resistance against flexion of the biasing member during the toe-off phase.

15. The prosthetic joint according to claim 9, wherein the second damper comprises a first end and a second end, and further defines an opening in the second end;

wherein the biasing member further includes an anterior surface that contacts the first end of the second damper during a toe-off phase of the prosthetic joint;

whereby the second damper provides resistance against flexion of the biasing member during the toe-off phase.

16. The prosthetic joint according to claim 15, wherein the second end of the second damper is adjustably arranged closer to and further from the anterior surface of the biasing member, thereby adjusting the resistance against the flexion of the biasing member during the toe-off phase.

* * * * *

UNITED STATES PATENT AND TRADEMARK OFFICE
CERTIFICATE OF CORRECTION

| | |
|---|---|
| PATENT NO. | : 7,618,463 B2 |
| APPLICATION NO. | : 11/483676 |
| DATED | : November 17, 2009 |
| INVENTOR(S) | : Magnus Oddsson, Vilhjalmur Freyr Jonsson and Christophe Guy Lecomte |

Page 1 of 1

It is certified that error appears in the above-identified patent and that said Letters Patent is hereby corrected as shown below:

Title page, item (*) Notice: should read as follows: Subject to any disclaimer, the term of this patent is extended or adjusted under 35 U.S.C. 154(b) by 646 days.

Please change "tower" to --lower-- in claim 10; column 16, line 42.

Signed and Sealed this

Tenth Day of August, 2010

David J. Kappos
*Director of the United States Patent and Trademark Office*